(12) United States Patent
Sovik et al.

(10) Patent No.: US 6,803,771 B2
(45) Date of Patent: Oct. 12, 2004

(54) PAVING MATERIAL ANALYZER SYSTEM AND METHOD

(75) Inventors: Robert A. Sovik, Clifton Park, NY (US); Richard N. Hosterman, Buskirk, NY (US); George G. Moross, Scotia, NY (US)

(73) Assignee: TransTech Systems, Inc., Schenectady, NY (US)

( * ) Notice: Subject to any disclaimer, the term of this patent is extended or adjusted under 35 U.S.C. 154(b) by 118 days.

(21) Appl. No.: 10/185,510

(22) Filed: Jun. 28, 2002

(65) Prior Publication Data

US 2002/0175691 A1 Nov. 28, 2002

Related U.S. Application Data

(63) Continuation-in-part of application No. 09/565,022, filed on May 4, 2000, now Pat. No. 6,414,497.

(51) Int. Cl.$^7$ .......................... G01R 27/28; G01R 27/26
(52) U.S. Cl. ........................................ 324/654; 324/663
(58) Field of Search ................................ 324/654, 663, 324/691; 400/83

(56) References Cited

U.S. PATENT DOCUMENTS

| | | |
|---|---|---|
| 3,400,331 A | 9/1968 | Harris |
| 3,671,857 A | 6/1972 | Bergmanis et al. |
| 3,694,742 A | 9/1972 | Bergmanis et al. |
| 3,781,672 A | 12/1973 | Maltby et al. |
| 3,784,905 A | 1/1974 | Blackwell |
| 3,882,381 A | 5/1975 | Gregory |
| 3,967,912 A | 7/1976 | Parker |
| 4,099,118 A | 7/1978 | Franklin et al. |
| 4,389,136 A | 6/1983 | Fehrenbach |
| 4,433,286 A | 2/1984 | Capots et al. |
| 4,468,610 A | 8/1984 | Hanson |

(List continued on next page.)

FOREIGN PATENT DOCUMENTS

FR 2593200 7/1987

OTHER PUBLICATIONS

Time domain technique for low frequency dielectric measurements, J. Phys. E: Sci. Instrum., vol. 13 (1980); Printed in Great Britain (month unavaliable).
Evaluation of Dielectric Measurement Apparatus For Determining Pavement Density, Jul. 1969, Prepared by Department of Highways State of Colorado–Planning and Research Division.
Atkins, R.T., Pangburn, T., Bates, R.E., and Brockett, B.E., "Soil Moisture Determinations Using Capacitance Probe Methodology," U.S. Army Cold Regions Research and Engineering Laboratory, Special Report 98–2, Jan. 1998.

*Primary Examiner*—Anjan Deb
*Assistant Examiner*—Timothy J. Dole
(74) *Attorney, Agent, or Firm*—Spencer K. Warnick; Hoffman, Warnick & D'Alessandro LLC

(57) ABSTRACT

A paving material analyzer system is disclosed that uses paving material impedance to determine paving material density. The invention also includes methods for analyzing paving material, in particular, determining paving material density. The paving material density can also be used to determine a percentage of maximum compaction. A paving material analyzer system is also disclosed that determines paving material density regardless of moisture presence on the paving material or a standoff distance of a sensor to the paving material. Sensor circuits providing for improved accuracy are also provided.

11 Claims, 8 Drawing Sheets

U.S. PATENT DOCUMENTS

| | | |
|---|---|---|
| 4,604,612 A | 8/1986 | Watkins et al. |
| 4,766,369 A | 8/1988 | Weinstein |
| 4,817,021 A | 3/1989 | Sowerby et al. |
| 4,933,853 A | 6/1990 | Musil et al. |
| 4,972,154 A | 11/1990 | Bechtel et al. |
| 5,051,026 A | 9/1991 | Sovik |
| 5,088,854 A | 2/1992 | Sovik |
| 5,134,380 A | 7/1992 | Jonas |
| 5,138,268 A | 8/1992 | Mulkey et al. |
| 5,210,500 A | 5/1993 | Pingel et al. |
| 5,213,442 A | 5/1993 | Sovik |
| 5,223,796 A | 6/1993 | Waldman et al. |
| 5,309,110 A | 5/1994 | O'Neill et al. |
| 5,363,051 A | 11/1994 | Jenstrom et al. |
| 5,378,994 A | 1/1995 | Novak et al. |
| 5,386,196 A * | 1/1995 | Jones et al. ................. 324/667 |
| 5,398,547 A | 3/1995 | Gerardi et al. |
| 5,436,565 A | 7/1995 | Gammell |
| 5,484,226 A | 1/1996 | Emerson et al. |
| 5,521,515 A | 5/1996 | Campbell |
| 5,551,288 A | 9/1996 | Geraldi et al. |
| 5,602,486 A | 2/1997 | Novak |
| 5,900,736 A | 5/1999 | Sovik et al. |
| 6,536,553 B1 * | 3/2003 | Scanlon ..................... 181/108 |

* cited by examiner

PAVING MATERIAL ANALYZER SYSTEM AND METHOD

This application is a continuation-in-part application of U.S. Ser. No. 09/565,022 filed May 4, 2002, to be issued Jul. 2, 2002 as U.S. Pat. No. 6,414,497.

BACKGROUND OF THE INVENTION

1. Technical Field

The present invention relates generally to paving material density analyzers. More particularly, the present invention relates to a paving material analyzer system and a method for analyzing paving material. The invention also relates to mechanisms for improving the accuracy of a paving material analyzer system and method.

2. Related Art

During paving operations, paving material is usually laid at about 75% of acceptable compaction. Acceptable compaction is a recommended level of compaction that reduces variations in the material, such as air voids, that can create potential defects in the paving material. It is highly advantageous to compact the paving material to a level as close to acceptable compaction as possible. Unfortunately, the level of compaction is not readily apparent by viewing the compacted paving material. In order to address this problem, measurement of dielectric properties of paving material is known to be very useful for determining material density, a key indicator of compaction level.

One pavement density indicator device is that of Blackwell, U.S. Pat. No. 3,784,905. Blackwell's device measures dielectric properties of the asphalt, which is representative of the change in density in the asphalt. The device of Blackwell has many disadvantages. For example, in order to obtain a reading, the Blackwell device must be moved at extremely slow speeds across the material being tested and, accordingly, requires an extended time period to provide a determination. The Blackwell device, due to its excessive weight, also requires a large sled frame (contact area) to be dragged across the pavement surface. Another disadvantage is limited adjustability of the depth of measurement of the device caused by the given set of electrodes only being able to vary the depth of measurement by changing the height of the electrodes. Yet another disadvantage is the inability to measure density when the paving material is wet.

In another apparatus, a nuclear source is used to determine density of pavement material. This device has a variety of obvious drawbacks. For instance, the device requires a licensed operator and a radiation shield (e.g., a lead enclosure). Furthermore, the device is non-adjustable for area, time-consuming in use, and heavy.

Another disadvantage of the above-described devices is their inability to vary the shape and area of the sensing area. Altering the shape and area of the sensing area is advantageous for determining the density in particular pavement attributes, e.g., dips, joints, odd shaped patches, etc.

Yet another disadvantage of the above-described devices is that their operation speed is relatively slow. It is therefore desired to have a system which is faster than those available.

Another shortcoming of current devices is inaccuracy created by, among other things, moisture on a surface of the paving material and a standoff distance of the sensor from the paving material surface.

In view of the foregoing there is a long felt need for a reliable paving material analyzer system and method for analyzing paving material. There is also a need for a system and method that can correct for moisture on the paving material. In addition, there is a need in the art for a system and method having increased accuracy.

SUMMARY OF THE INVENTION

The invention overcomes the above shortcomings by providing in a first aspect of the invention, a paving material analyzer system comprising: a sensor; an electronic circuit operatively coupled to the sensor to generate an electrical field from the sensor proximate the paving material; and a data analyzer that determines a density of the paving material based on the effect of impedance characteristics of the paving material on the electrical field.

A second aspect of the invention provides a method for analyzing paving material comprising the steps of: determining an impedance of the paving material; and determining the density of the paving material based on the impedance determination of the paving material.

A third aspect of the invention provides a paving material analyzer system comprising: means for determining an impedance of the paving material; and means for determining the density of the paving material based on the impedance determination of the paving material.

In a fourth aspect of the invention is provided a paving material analyzer system comprising: a sensor; an electronic circuit operatively coupled to the sensor to generate an electrical field from the sensor proximate the paving material; and a density determining data analyzer that determines a density of the paving material regardless of moisture presence on the paving material.

A fifth aspect of the invention is directed to a paving material analyzer system comprising: an electronic circuit including an inductor adapted to null a capacitive reactance portion of an impedance reading of the paving material leaving a non-reactive portion; and a data analyzer operatively coupled to the electronic circuit that determines: a total impedance of the paving material based on the non-reactive portion, a known inductive reactance and a known operating frequency of the electronic circuit, and a density of the paving material based on the total impedance.

A sixth aspect of the invention is directed to a paving material analyzer system comprising: means for measuring an impedance of the paving material and nulling a capacitive reactance portion of the impedance; means for analyzing data operatively coupled to the means for measuring, the means for analyzing determining: a total impedance of the paving material based on a non-reactive portion of the impedance, a known inductive reactance portion of the impedance and a known operational frequency of the means for measuring, and a density of the paving material based on the total impedance.

A seventh aspect of the invention provides a method for analyzing paving material comprising the steps of: determining an impedance of the paving material; determining a capacitance of a space between a sensor and the paving material; and determining the density of the paving material based on the impedance determination of the paving material and the capacitance of the space.

An eighth aspect of the invention is directed to a paving material analyzer system having a sensor operatively couple to an electronic circuit for generating an electric field proximate paving material and a data analyzer for determining a density of the paving material, the system comprising: a standoff distance corrector that corrects the density for a distance of the sensor to the paving material.

The foregoing and other features and advantages of the invention will be apparent from the following more particular description of preferred embodiments of the invention.

BRIEF DESCRIPTION OF THE DRAWINGS

The preferred embodiments of this invention will be described in detail, with reference to the following figures, wherein like designations denote like elements, and wherein.

DESCRIPTION OF THE PREFERRED EMBODIMENTS

While the preferred embodiments will be described in conjunction with the paving environment, other applications of the invention will become apparent to those skilled in the art. The limited description is intended only for ease of explaining the construction and operation of the device. Accordingly, "paving material" should be interpreted broadly to include all varieties of asphalt, cement, concrete, soil, sand, stones, bituminous material and all other forms of in-place material.

Figure 1:
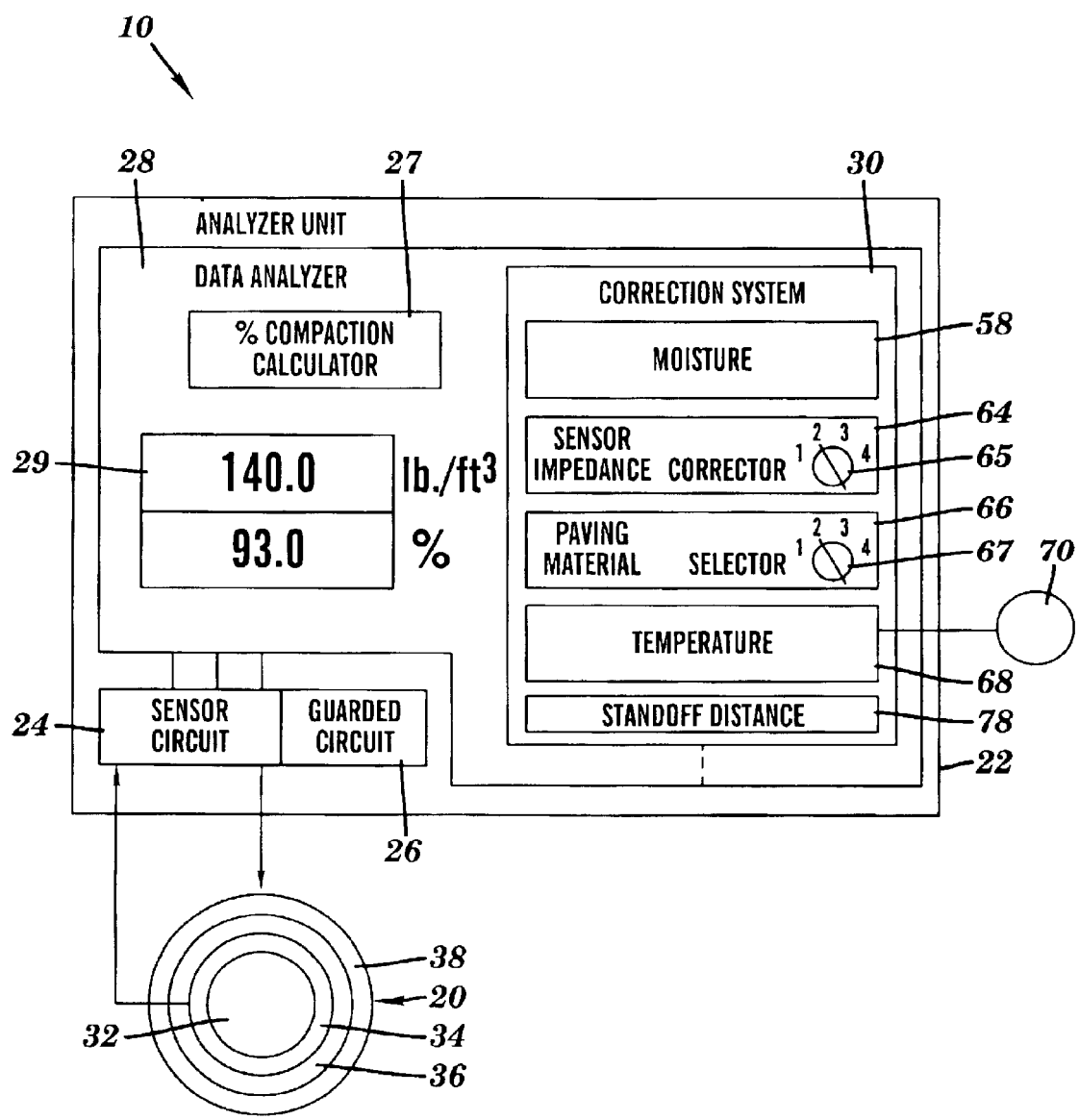
FIG. 1 shows a schematic view of a paving material analyzer system.

Referring to FIG. 1, a schematic view of a paving material analyzer system 10 is shown. System 10 includes a sensor 20 and an analyzer unit 22. Analyzer unit 22 preferably has a sensor circuit 24 and a data analyzer 28. Sensor circuit 24 is an electronic circuit that: 1) applies an electric potential to sensor 20 to generate, or transmit, an electrical field; and 2) receives the electrical field. Sensor circuit 24 preferably includes a guarded circuit 26. As will be described in greater detail below, data analyzer 28 may include a percentage compaction calculator 27, a display 29 and a correction system 30.

Figure 2:
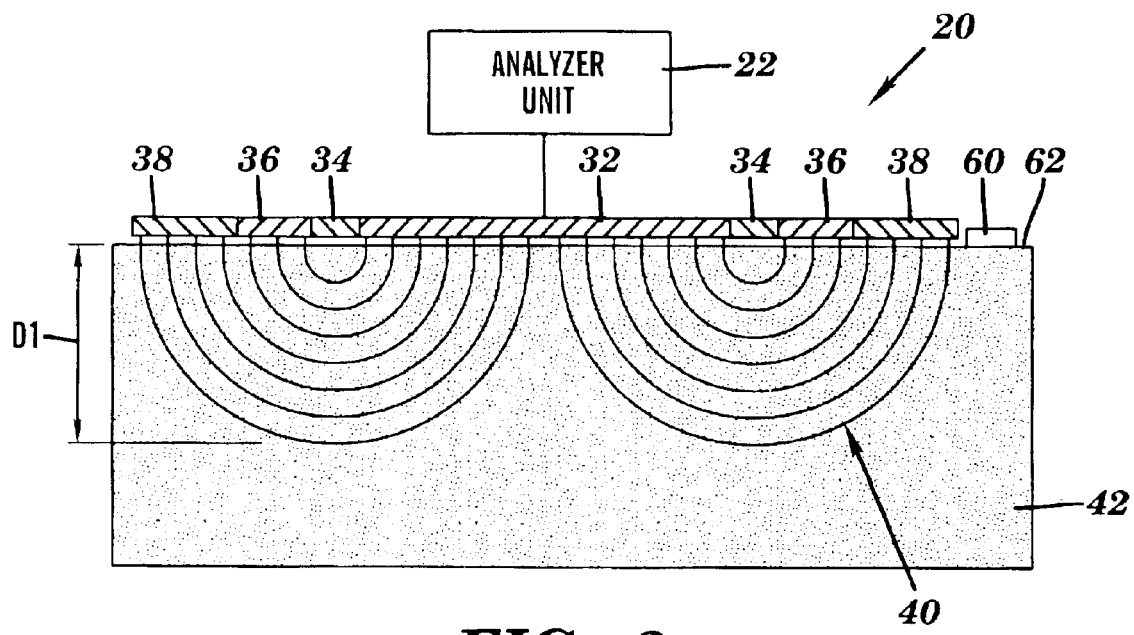
FIG. 2 shows a cross-sectional view of the system of FIG. 1 in use.

An exemplary structure of sensor 20 is shown in FIGS. 1 and 2. Sensor 20 may include an active inner element 32 surrounded by an intermediate ground element 34 which is surrounded by a first outer element 36 and a second outer element 38. As shown in FIG. 2, an electrical field 40 is created proximate paving material 42 by applying an electric potential (from electronic circuit 24 shown in FIG. 1) through sensor 20. Electrical field 40 is transmitted from sensor 20 via element 38 and/or element 36 into adjacent paving material 42. Sensor 20 may be in contact with paving material 42 during use. Inner element 32 then receives this electrical field signal from paving material 42, the signal having been altered by the impedance characteristics of paving material 42. Each of elements 32, 34, 36, 38 may be constructed of any conducting material, but are preferably made of copper, aluminum or steel. Elements are held together and insulated from each other by a non-conductive material such as an epoxy.

Figure 3:
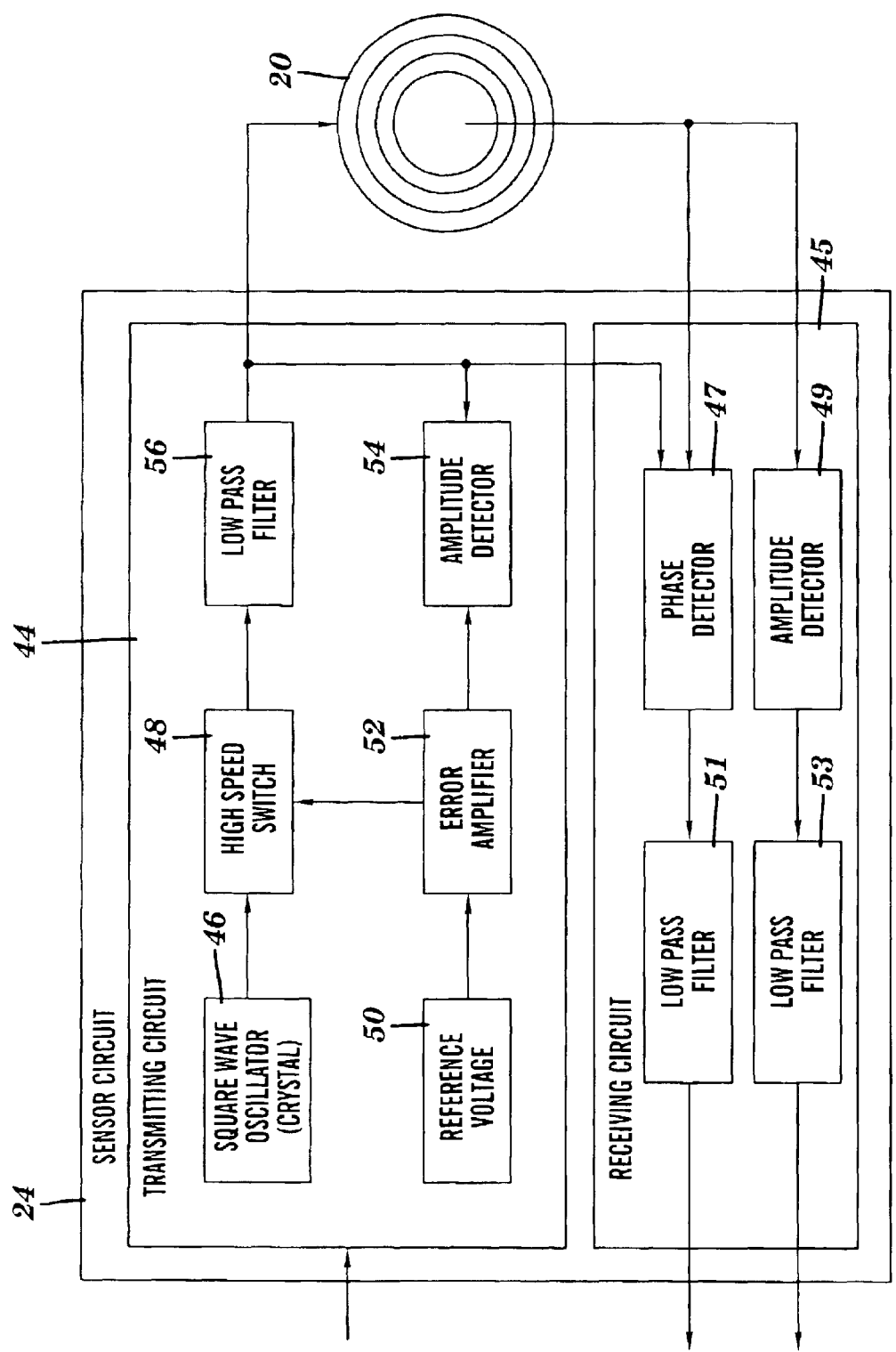
FIG. 3 shows a circuit diagram of a sensor circuit.

Turning to FIG. 3, in one embodiment, sensor circuit 24 preferably includes a transmitting circuit 44 and a receiving circuit 45. While preferred embodiments of these circuits have been illustrated, it should be noted that these circuits 24, 44, 45 may take a variety of forms. The embodiments disclosed for each should, therefore, not be taken as limiting the invention to any particular number or form of circuitry.

In the exemplary circuits shown in FIG. 3, transmitting circuit 44 is a constant voltage source circuit. Circuit 44 includes a square wave oscillator (crystal) 46 coupled to a high speed switch 48. A reference voltage 50 is supplied to an error amplifier 52 that is also coupled to high speed switch 48. An amplitude detector 54 is also coupled to error amplifier 52. A low pass filter 56 is provided at an output of high speed switch 48. Output of low pass filter 56 is the constant voltage sine wave output for sensor 20. Amplitude detector 54 also receives the output of low pass filter 56 and maintains the constant voltage output. The output to sensor 20 preferably has a frequency in the range of 200 kHz to 15 MHz. It should be recognized that while a preferred constant voltage source circuit has been illustrated, other systems that provide a constant voltage source are also possible. Accordingly, the invention should not be limited to any particular form of constant voltage source circuitry.

In the exemplary receiving circuit 45, a phase detector 47 and an amplitude detector 49 receive the electrical field signal back from sensor 20. Phase detector 47 is also coupled to an amplitude detector 54, which it may share with transmitting circuit 44. Phase detector 47 and amplitude detector 49 feed to a low pass filter 51 and a low pass filter 53, respectively. The outputs of low pass filters 51, 53 are coupled to data analyzer 28 for analysis of the electrical field signal.

Returning to FIG. 1, regardless of the type of sensor circuit 24 used, it is preferred that a guarded circuit 26 is included so sensor circuit 24 and sensor 20 are guarded. In this setting, guarded circuit 26 would be coupled to an additional element 74, shown in FIG. 5. Element 74 acts as a guard element for sensor 20. It has been found that this promotes accuracy because determinations are not subject to stray fields.

As also shown in FIG. 1, system 10 includes a data analyzer 28. In one embodiment, data analyzer 28 is a microcomputer configured to determine the density of paving material 42 based on the effect of the impedance characteristics of paving material 42 on electrical field 40. In particular, data analyzer 28 determines an impedance value of paving material 42, e.g., by comparing a transmitted electrical field signal versus a received electrical field signal that has passed through paving material 42. Data analyzer 28 uses the impedance value to determine a density value of paving material 42. Impedance has been found to be a more useful measure of density than predecessor systems' use of capacitance.

Data analyzer 28 is capable of determining paving material density in terms of: 1) variations in paving material density across a measurement area, and 2) actual density indications. In order to determine the density of paving material 42 in terms of variations in density, variations in impedance of electrical field 40 created by the impedance characteristics of paving material 42 are tracked.

In a preferred embodiment, however, data analyzer 28 is configured to mathematically provide actual density determinations, e.g., 140 lb/ft$^3$, and output them to a display 29. Density mathematical algorithms used to determine actual density indications may be created by modeling empirical data. Empirical data may be produced, for example, by calibrating a given sensor at a preferred operational setting with regard to specific types of paving material at known compaction densities. Mathematical modeling of the relationships between the measured impedance and known compaction densities results in a way to accurately determine density from an impedance of a specific type of paving material. Different mathematical algorithms can be created for different paving material and/or different sensors to make system 10 more accommodating, as will be described in more detail below. As one with skill in the art will appreciate, there may be other mechanisms other than mathematical modeling to determine actual density values. For instance, it may be possible to simply use the empirical data as a database to determine density, i.e., use the data as a lookup table.

Data analyzer 28 may also include a percentage compaction calculator 27 that calculates a percentage of maximum compaction, or percentage of air voids, of a particular paving material from the determination of density. The percentage can then be outputted to display 29. The relationship of density to a compaction percentage may be determined in many ways. One example method is by dividing the density determination by a known maximum compaction density for a particular paving material 42 that has been inputted to data analyzer 28. Data analyzer 28 may also be configured to calculate a compaction percentage without a separate calculator 27, i.e., as part of its operations discussed above.

As shown in FIG. 1, data analyzer 28 may also include a correction system 30. Correction system 30 may include a number of correction subsystems 58, 64, 66, etc. for making corrections to an impedance determination and, hence, determination of density and percentage compaction.

A first preferred correction subsystem 58 is a moisture corrector that corrects for moisture 60 on a top surface 62 of paving material 42, as shown in FIG. 2. In particular, it has been found that an increase in the phase angle of the measured impedance is indicative of increased moisture 60 on a top surface 62 of paving material 42. Similarly to the overall density mathematical algorithms discussed above, moisture correction mathematical algorithms can be created by modeling empirical data of moisture content. A moisture content mathematical algorithm can then be appropriately factored into the density mathematical algorithm to correct for moisture content, i.e., by removing a moisture content factor from the density mathematical algorithm. As a result, more accurate density determinations are possible. As with the density mathematical algorithms, a number of moisture content mathematical algorithms can be created for different paving material and/or different sensors to make system 10 more accommodating. With the above moisture corrector 58, a system 10 can determine the density of paving material based on the effect on the electrical field caused by the impedance characteristics of the paving material and regardless of moisture presence on the paving material.

Any impedance determination completed by system 10 automatically includes a quantity that is attributable solely to sensor 20, i.e., a sensor impedance. Accordingly, inaccuracies may result unless the sensor impedance is removed from the overall impedance determination. Sensor impedance may be created by a number of factors such as the type of a protective coating (not shown) that may be applied to sensor 20 and/or any air void that may be provided between a protective coating and sensor elements 32, 34, etc. Where a given system 10 will be used on only one paving material 42 and will not have a changeable sensor 20, a pre-set sensor impedance correction factor can be used to remove the pre-determined sensor impedance from the density mathematical algorithms. However, where system 10 may be used with different sensors 20, a sensor impedance corrector 64 is preferably provided as a second correction subsystem to remedy the problem. In this setting, a sensor impedance correction factor for each sensor may be predetermined, and a sensor selector 65 (FIG. 1) may be provided for choosing a given sensor and correction factor. Data analyzer 28 could then automatically correct for sensor impedance regardless of the sensor used. It should be recognized that other mechanisms for inputting a sensor impedance correction factor may be provided and not depart from the spirit of this invention. For instance, each sensor 20 may have a sensor impedance correction factor indicated thereon for input by a user into system 10. As an alternative, rather than simply providing a sensor impedance correction factor, sensor impedance corrector 64 may also operate to implement different density mathematical algorithms for each sensor that automatically account for sensor impedance.

Another correction subsystem 66 that may be provided is for selection of a particular paving material 42. For instance, if a particular paving material 42 is known to require special treatment by system 10, subsystem 66 could provide a paving material selector 67 (FIG. 1) so data analyzer 28 can automatically correct problems that may cause inaccuracies. In this setting, each common paving material would have a predetermined correction factor(s) associated therewith. Alternatively, paving material selector 67 may operate to implement different density mathematical algorithms for each paving material that automatically account for any necessary special treatment.

A temperature corrector 68 may also be provided as a correction subsystem. Temperature corrector 68 would include a thermometer 70 and would create a correction factor by way of a correction algorithm. For instance, it has been found that an increase in paving material temperature results in a higher density determination and that the density determination can be corrected by subtracting a density value proportional to paving material temperature.

Figure 4:
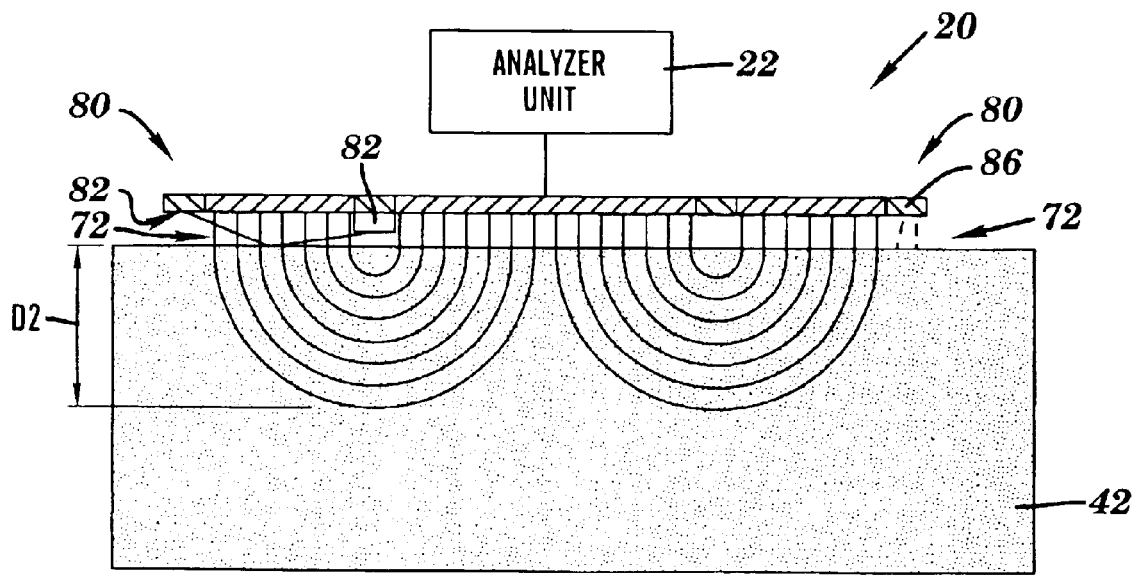
FIG. 4 shows a cross-sectional view of an alternative operational setting of the system of FIG. 1.
Figure 8:
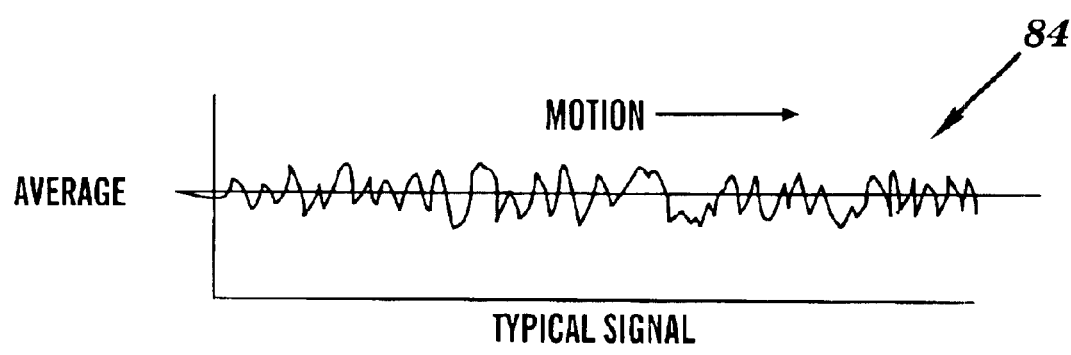
FIG. 8 shows a paving material profile.

Another correction subsystem that may be provided is a standoff distance corrector 78. As shown in FIG. 4, it is contemplated that sensor 20 can operate at a standoff distance from paving material 42. Capacitance caused by gap 72 between sensor 20 and paving material 42 can adversely affect the impedance determination and, hence, the density determination if not corrected. To remedy this problem, an additional standoff distance corrector 78 can be added that uses, for example, an RC oscillator system similar to that discussed in U.S. Pat. No. 5,900,736, which is hereby incorporated by reference. In another embodiment, shown in FIG. 4, a standoff distance corrector may include a mechanism 80 for measuring surface characteristics (e.g., texture, uniformity and segregation) and the distance of sensor 20 to paving material 42. In one embodiment, standoff distance corrector 78 (FIG. 1) includes a laser probe 82 (FIG. 4), which is focused on paving material 42. The reflection of the laser can be used to determine the distance from sensor 20 to paving material 42. Although the laser shown is set to detect an angle, which can be used to determine the distance, it should be recognized that other arrangements using a laser are possible. Laser probe 82 can also be used to determine a paving material surface characteristic profile 84, as shown in FIG. 8, as sensor 20 moves over paving material 42. Profile 84 may be used to sense characteristics such as segregation of paving material 42 and the general quality of the surface. Profile 84 may also be used to determine the distance of sensor 20 to paving material 42 by averaging the distances indicated in the profile. As an exemplary alternative (also shown in FIG. 4), standoff distance corrector 78 (FIG. 1) may include an ultrasonic unit 86. Once the distance is determined, a size of the space is determined and the capacitance due to the space can be determined and an appropriate correction to the total impedance made, thus giving a more accurate determination of the density of paving material 42. The capacitance due to the space may be determined by mathematical modeling, lookup tables, etc., similarly to the density calculations discussed above. Although exemplary mechanisms 80 for measuring the distance and surface characteristics have been described and illustrated, any now known or later developed device for providing such function can be used within the scope of the invention.

It should be recognized that, in some instances, maintaining sensor 20 parallel to paving material 42 may be required for accurate capacitance determination of space 72. However, undulations and the like in paving material 42 may make this difficult. One remedy for this problem includes the provision of additional mechanisms 80, for measuring the distance from sensor 20 to paving material 42. Using a number of mechanisms 80, an angle(s) of sensor 20 relative to paving material 42 can be determined such that a correction(s) can be implemented in the capacitance calculation. Another remedy includes controlled positioning of sensor 20 to maintain it substantially parallel to paving material 42, e.g., by use of one or more servo-mechanisms. This latter remedy may also require additional mechanisms 80 to determine when sensor 20 is not parallel with paving material 42. Other remedies may also be implemented to address this problem.

It is understood that analyzer unit 22 and its components can be realized in hardware, software, or a combination of hardware and software. Furthermore, analyzer unit 22 may be realized in a centralized fashion in one computer system, or in a distributed fashion where different elements are spread across several interconnected computer systems, e.g., data analyzer 28 can split into an impedance determining unit, a density determining unit, etc. Any kind of computer system—or other apparatus adapted for carrying out the methods described herein—is suited. A typical combination of hardware and software could be a general purpose computer system with a computer program that, when being loaded and executed, controls data analyzer 28 such that it carries out the methods described herein. The present invention can also be embedded in a computer program product, which comprises all the features enabling the implementation of the methods described herein, and which—when loaded in a computer system—is able to carry out these methods.

Computer program, software program, or planning software, in the present context mean any expression, in any language, code or notation, of a set of instructions intended to cause a system having an information processing capability to perform a particular function either directly or after either or both of the following: (a) conversion to another language, code or notation; (b) reproduction in a different material form.

Figure 6:
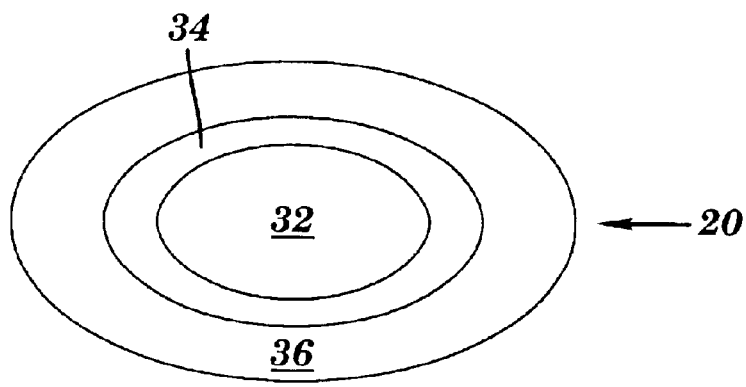
FIG. 6 shows a detail view of a second alternative embodiment of a sensor.
Figure 7:
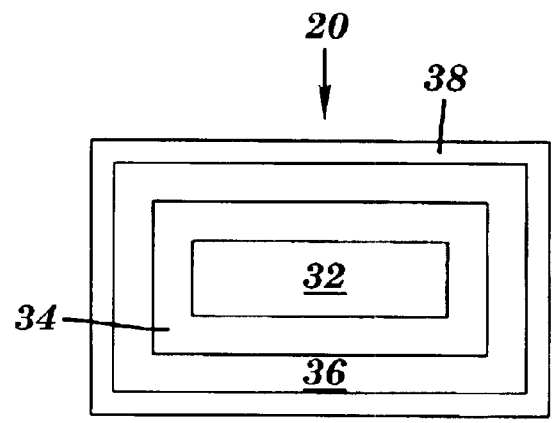
FIG. 7 shows a detail view of a third alternative embodiment of a sensor.
Figure 5:
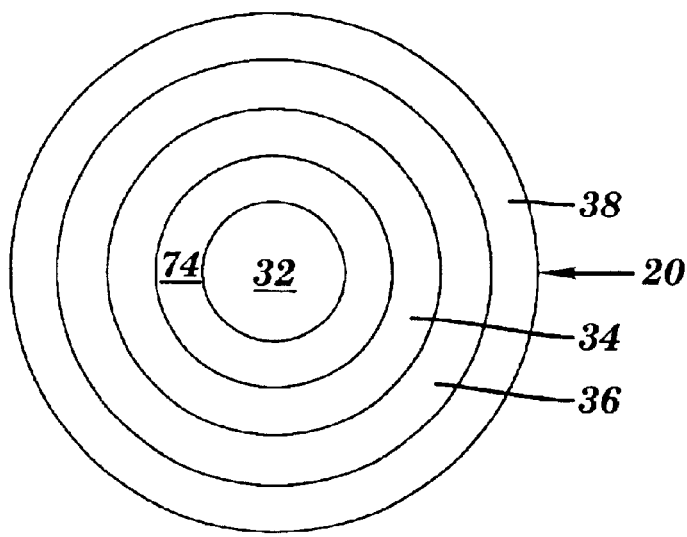
FIG. 5 shows a detail view of a first alternative embodiment of a sensor.

Referring to FIGS. 5–7, a variety of sensors 20 having different numbers of elements are shown. For instance, a sensor 20 shown in FIG. 5 has an additional guard element 74, and a sensor 20 shown in FIG. 6 has outermost element 38 removed. When guard element 74 is provided, it is coupled to guard circuit 26 so that sensor circuit 24 and sensor 20 are guarded. Additional elements surrounding those described above, and structured in similar fashion as those above, may be used to make system 10 more stable. Additional elements are advantageous to make the electrical field more uniform or compensate for other parameters that may interfere with impedance measurement, e.g., known electromagnetic interference.

FIGS. 5–7 also illustrate how the shape and size of sensors can be selectively different. The examples shown are a circular shape in FIG. 5; an elliptical shape in FIG. 6; and a polygonal, i.e., rectangular, shape in FIG. 7. Adjustability of the shape and size of sensor 20 is advantageous to system 10 because the shape and size of sensor 20, inter alia, dictates the depth of penetration and area of electrical field 40 and, accordingly, the volume of the field of test. For instance, as illustrated in FIG. 4, operation of a smaller sized sensor 20 allows the depth of penetration to be reduced to D2 as opposed to the depth D1 shown in FIG. 2. Being able to accurately control the depth of penetration prevents imprecise determinations when the signal penetrates through a new lift coat into an underlying surface that may not have the same density.

Changing the shape and size of sensor 20 also allows for a variation of the shape of the area tested. For instance, when a user wishes to determine density at a joint between two new lift coats, he can now use, for example, a long rectangular sensor as shown in FIG. 7 to assure accurate sensing along the joint.

Although FIGS. 5–7 show sensors in three preferred shapes, sensor 20 may take a variety of alternative shapes. Furthermore, although the embodiments shown are fixed in nature, it is also envisioned to provide a sensor with an adjustable shape.

The provision of a constant voltage source circuit enables system 10 to detect material density with more accuracy and reliability than related art devices or the constant current source disclosed in U.S. Pat. No. 5,900,736. Constant voltage source circuit in sensor circuit 24 also provides a lower impedance sensor, which provides a stable system that is not alterable by environmental factors, e.g., electromagnetic interference. Accordingly, the potential for mismeasurement is reduced. Furthermore, system 10 is lightweight and allows for instantaneous and continuous determinations that reduces paving time. The provision of correction system 30 and its related subsystems makes system 10 even more accurate.

Figure 9:
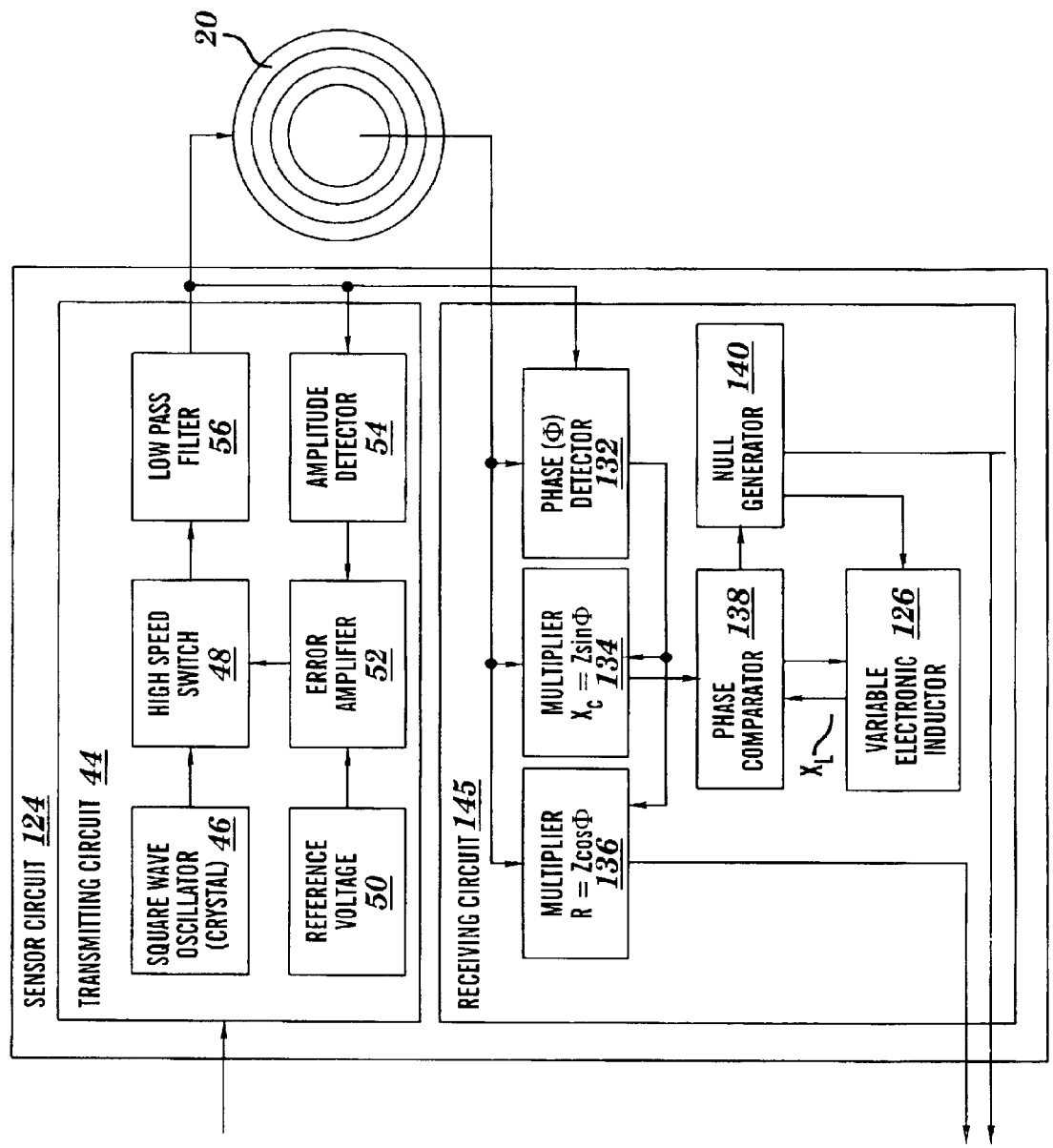
FIG. 9 shows a circuit diagram of an alternative sensor circuit.

Referring to FIG. 9, an alternative sensor circuit 124 may include an inductor 126 that allows for improved accuracy. In one embodiment, inductor 126 is a variable electronic inductor, e.g., based on an active operational amplifier circuit. Inductor 126 as controlled by data analyzer 28 is adapted to null a capacitive reactance portion of the impedance by applying a known inductive reactance. That is, inductor 126 is configured to be variable by data analyzer 28, e.g., by applying a known voltage, to cancel the capacitive reactance portion of the impedance leaving only the non-reactive portion of the impedance, i.e., a resistance portion. In this setting, data analyzer 28 functions to determine a total impedance of paving material 42 based on the non-reactive portion, the known inductive reactance portion and a known operating frequency of circuit 124. In particular, data analyzer 28 can determine the value of the unknown capacitance from the known value of the inductive reactance portion and the operational frequency. The total impedance is then based on the capacitive reactance, inductive reactance and the non-reactive portion (resistance). As discussed above, the density of the paving material can be determined based on the total impedance.

In one embodiment, shown in FIG. 9, alternative sensor circuit 124 is implemented with substantially the same transmitting circuit 44 as that shown in FIG. 3. Receiving circuit 145 is provided with a phase ($\Phi$) detector 132, a first multiplier 134 and a second multiplier 136 that receive the electrical field signal from sensor 20. Phase detector 132 is also coupled to an amplitude detector 54, which it may share with transmitting circuit 44. Phase detector 132 also feeds to each multiplier 134 and 136. First multiplier 134 feeds a capacitive reactance signal ($X_c = Z \sin \Phi$) to a phase comparator 138. Phase comparator 138 feeds to a null generator 140 and variable electronic inductor 126. Null generator 140 also feeds to variable electronic inductor 126. Inductor 126 feeds back to phase detector 138 an inductive reactance signal $X_L$. Second multiplier 136 feeds back to data analyzer 28 a non-reactive portion (resistance) of impedance ($R = Z \cos \Phi$). Null generator 140 also feeds back to data analyzer 28 a signal that can be used to determine the inductive reactance portion and, hence, the resultant capacitive reactance of the paving material 42. As discussed above, data analyzer 28 calculates total impedance and density based on the above information.

Figure 10:
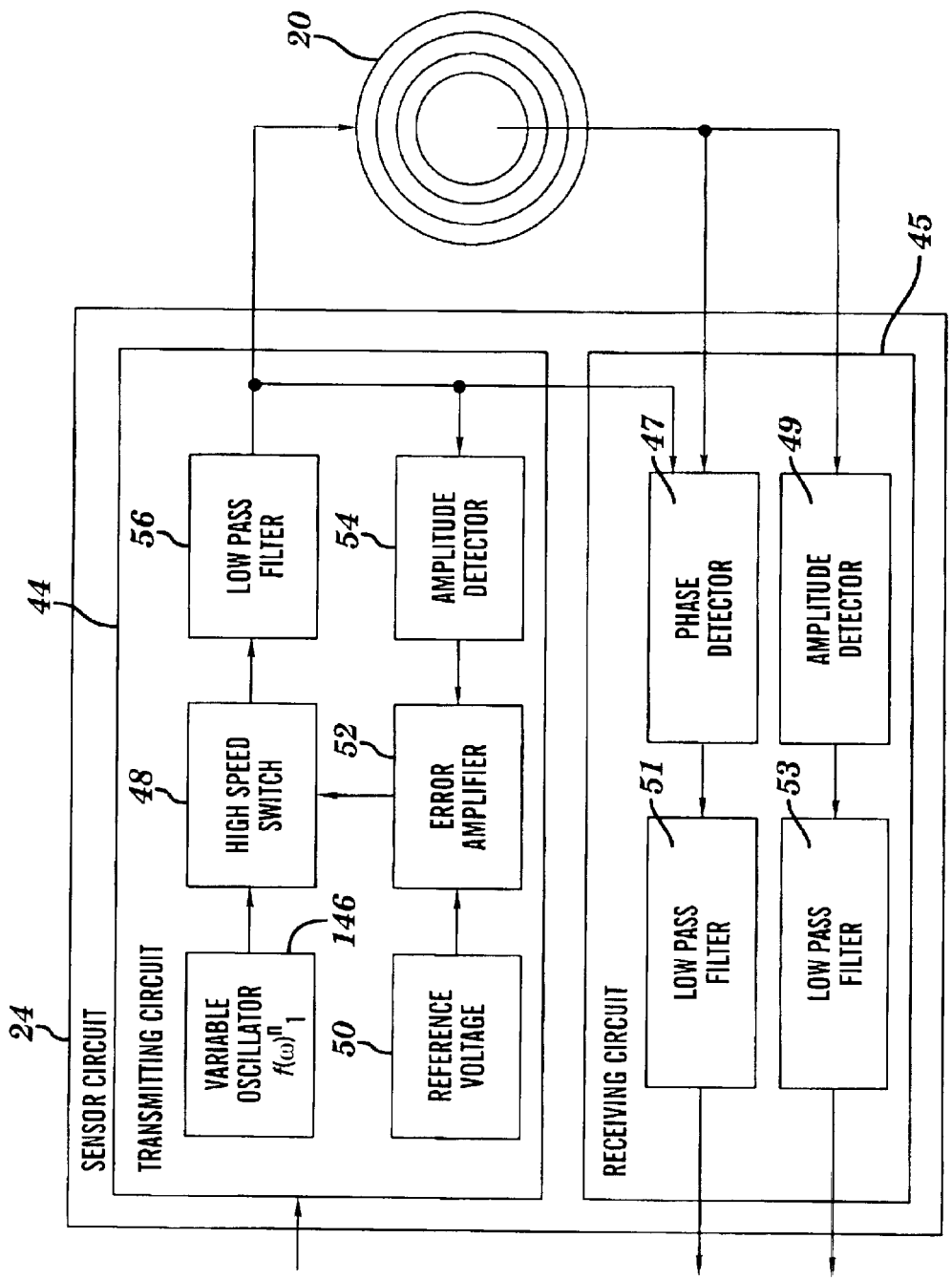
FIG. 10 shows a circuit diagram of another alternative sensor circuit.
Figure 11:
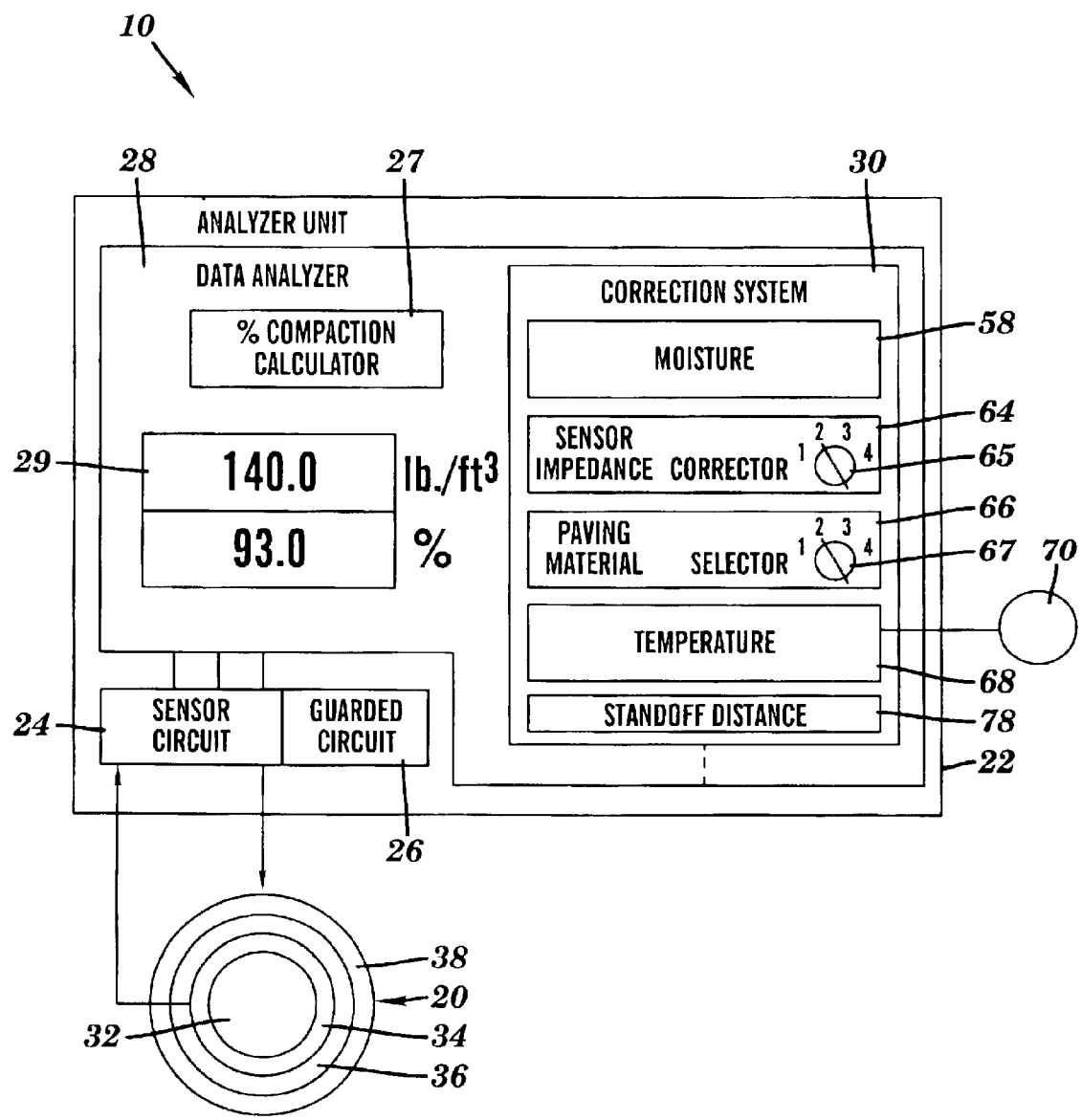
FIG. 11 shows a circuit diagram of another alternative sensor circuit.

Referring to FIGS. 10 and 11, square wave oscillator 46 of transmitting circuit 44 may be replaced in the above sensor circuits 24 (FIG. 3) and 124 (FIG. 9) with a variable oscillator 146 ($f(\omega)_1{}^n$), which provides increase applicability. Frequency can then be varied, for example, in a sweep fashion or multiplexed to provide a number of sequential frequency signals. In any case, each of the other parts shown are configured to operate at whatever frequency or range is implemented. FIG. 10 shows a variable oscillator 146 implemented on sensor circuit 24 of FIG. 3, and FIG. 11 shows a variable oscillator 146 implemented on sensor circuit 124 of FIG. 9.

The invention also includes a method for analyzing paving material using the above-described system(s). The method includes the steps of determining an impedance of the paving material; and determining the density of the paving material based on the impedance determination of the paving material. The step of determining an impedance may include: providing a sensor; applying an electric potential through the sensor to generate an electrical field proximate the paving material; receiving the electrical field from the paving material; and determining an impedance of the paving material based on the effect of impedance characteristics of the paving material on the electrical field.

The step of determining an impedance may also include correcting the determination for an impedance of the sensor, and correcting the determination for moisture on a top surface of the paving material. The correction for moisture is preferably provided by monitoring a phase angle of the impedance to determine moisture on a top surface of the paving material, and correcting the impedance determination accordingly. An alternative step would be to calculate a percentage of full compaction of the paving material.

An alternative method for analyzing paving material may include the steps of: determining an impedance of the paving material; determining a capacitance of a space between a sensor and the paving material; and determining the density of the paving material based on the impedance determination of the paving material and the capacitance of the space. The correction steps discussed above may also be included as part of this alternative method.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention as defined in the following claims.

We claim:

1. A method for analyzing paving material comprising the steps of:
   determining an impedance of the paving material;
   determining a capacitance of a space between a sensor and the paving material by measuring a distance of the sensor to the paving material and determining the capacitance based on the distance; and
   determining the density of the paving material based on the impedance determination of the paving material and the capacitance of the space.

2. The method of claim 1, wherein the step of determining an impedance of the paving material includes:
   providing a sensor;
   applying an electric potential to the sensor to generate an electrical field proximate the paving material;
   receiving the electrical field from the paving material; and
   determining an impedance of the paving material based on the effect of impedance characteristics of the paving material on the electrical field.

3. The method of claim 2, wherein the step of determining the impedance of the paving material includes nulling a capacitive reactance portion of the impedance.

4. The method of claim 1, wherein the step of determining an impedance of the paving material includes correcting the determination for an impedance of the sensor.

5. The method of claim 1, wherein the step of determining an impedance of the paving material includes correcting the determination for moisture on a top surface of the paving material.

6. The method of claim 5, wherein the step of correcting includes monitoring a phase angle of the impedance to determine moisture on a top surface of the paving material.

7. A paving material analyzer system having a sensor operatively coupled to an electronic circuit for generating an electric field proximate paving material end a data analyzer for determining a density of the paving material, the system comprising;
   a standoff distance corrector that corrects the density for a distance of the sensor to the paving material,
   wherein the standoff distance corrector includes a distance measurer configured to measure the distance of the sensor to the paving material and the standoff distance corrector determines a capacitance based on the distance.

8. The system of claim 7, wherein the distance measurer includes a laser probe.

9. The system of claim 8, wherein the standoff distance corrector also determines a paving material surface profile.

10. The system of claim 7, wherein the distance measurer includes a paving material contact and a Hall effect sensor coupled thereto.

11. The system of claim 7, wherein the electronic circuit includes means for determining an impedance of the paving material and nulling a capacitive reactance portion of the impedance.

* * * * *